United States Patent [19]

Chappel

[11] Patent Number: 5,087,615
[45] Date of Patent: Feb. 11, 1992

[54] NOVEL METHOD OF OVULATION INDUCTION IN HUMANS

[75] Inventor: Scott C. Chappel, Boston, Mass.

[73] Assignee: Applied Research Systems ARS Holding N.V., Curacao, Netherlands

[21] Appl. No.: 324,949

[22] Filed: Mar. 17, 1989

[51] Int. Cl.$^5$ .................. A61K 37/00; A61K 37/24; C07K 7/10
[52] U.S. Cl. .................... 514/21; 514/12; 435/69.4; 530/313; 530/324
[58] Field of Search .............. 435/69.4; 514/12, 21; 530/313, 324

[56] References Cited

U.S. PATENT DOCUMENTS 4,589,402  5/1986  Hodgen et al. .............. 128/1 R
4,923,804  5/1990  Reddy et al. ............... 435/69.4

FOREIGN PATENT DOCUMENTS

WO87/06466  11/1987  PCT Int'l Appl. .
WO88/10270  12/1988  PCT Int'l Appl. .

OTHER PUBLICATIONS

Vaitukaitis, C.A. 75:126325b.
Grodecka, C. A. 94:11840r.
Morell, C. A. 74:96321g.
Chappel, Endocrinology 115:452(1984).

Primary Examiner—Lester L. Lee
Assistant Examiner—Avis Davenport
Attorney, Agent, or Firm—Stephan P. Williams

[57] ABSTRACT

Disclosed are novel methods for inducing human ovulation by administering sequentially a plurality of recombinant FSH preparations, each of which have a distinguishable plasma half-life.

9 Claims, No Drawings

NOVEL METHOD OF OVULATION INDUCTION IN HUMANS

FIELD OF INVENTION

This invention deals with human gonadotropins and more specifically promotes a novel treatment method for ovarian follicular stimulation and compositions useful therefore.

BACKGROUND OF THE INVENTION

Approximately 20% of all married couples exhibit some form of infertility. A significant portion of the women in this group experience hypothalamic ammenohrea. For almost twenty years these women have been treated with a commercial preparation of the human gonadotropins (Pergonal TM of Serono), luteinizing (LH) and follicle stimulating hormone (FSH) obtained by purification of urine obtained from post-menopausal women. In general, this treatment is highly effective in stimulating folliculogenesis and steroidogenesis in the otherwise quiescent ovary. Indeed, major complications of this treatment result from the fact that this preparation works too well. The ovary can become hyperstimulated, which may result in multiple ovulations or even a life-threatening condition.

It is an aspect of the present invention to provide an improved therapeutic and treatment method which substantially reduces or eliminates such complications.

During a normal menstrual cycle, all but one of a large crop of developing follicles becomes atretic. When an artificial cycle is created by the administration of gonadotropin preparations, multiple ovulations are observed.

Although infertile couples welcome a therapy to induce the ovulatory process, they are rarely enthusiastic over the prospect of carrying 3–7 fetuses to term. An analysis of clinical, ethical and financial aspects of this complication of gonadotropic therapy is beyond the scope of this application but clearly represents issues which this invention seeks to obviate. Scientists are now beginning to understand the mechanisms responsible for the selection of the dominant follicle (the ovarian structure responsible for shedding one mature ova to be fertilized at mid cycle) which should help to reduce the occurrence of multiple pregnancies in conventionally treated woman.

The following brief summary of this area of research may prove useful in understanding the present invention.

The maturation and ultimate ovulation of only one of a large cohort of follicles is thought to be the result of continuous gonadotropin support to one follicle at the expense of all others (Richards, Rec. Prog. Hormone Res. 35:343 (1979)). Different growth rates, blood supply, and/or secretion of stimulatory and inhibitory paracrine factors by the individual follicles have all been shown to play a role in this phenomenon. However, gonadotropin support to the ovary is an essential part of the selection process. During a normal menstrual cycle, the hypothalamus, pituitary and ovaries exist in a dynamic equilibrium. As the ovarian follicles grow and mature, they release substances that are recognized by the hypothalamus and pituitary. These hormones regulate subsequent pituitary secretions to create an endocrine environment that supports the continued growth of only one follicle. Clearly the conventional therapeutic regimen of continuous administration of exogenous gonadotropins does not replicate this finely-tuned endocrine interaction.

It is yet another aspect of the present invention to more closely simulate the natural endocrine interactions.

As stated above, gonadotropin stimulation plays a key role in follicular development and ovulation. The regulation of the absolute amount of gonadotropin secreted is one mechanism that results in the selection of a dominant follicle. The pituitary gland also adjusts the chemical composition of the gonadotropin molecules secreted during the preovulatory period. As the follicle matures, the survival time of the FSH molecule in circulation decreases. Through these mechanisms, the amount and duration of the FSH stimulus provided to the ovary is shortened. As a result, only the largest and fastest growing follicle receives continuous support.

It is now well accepted that both LH and FSH circulate as a heterogeneous population of molecules. Individual FSH isoforms exhibit identical amino acid sequences but differ in the extent to which they are post-translationally modified. As a result of these modifications, the isoforms exhibit differences in overall charge, degree of sialic acid (a terminal sugar) or sulfate incorporation, receptor binding affinity and plasma half-life (Chappel et al., Endocrine Reviews 4:179 (1983); Snyder et al. Mol. Cell. Endocrin. 54:115 (1987)).

It has been discovered that these forms are separable from each other on the basis of their overall charge. All of the isoforms exhibit FSH biologic activity. Forms that exhibit a greater net negative charge are more heavily sialylated, exhibit a longer metabolic clearance rate and a greater biologic activity due to their extended plasma survival time.

Analysis of the FSH isohormones present within commercial preparations of Pergonal has revealed the domination by the more heavily sialylated (more acidic) forms (Harlin et al., Fert. Steril. 46:1055 (1986); Chappel et al., Acta Endocrinol. 113:311 (1986)). This confirms expectations since the Pergonal preparation is derived from the urine of post-menopausal women. The pituitary gland is known to respond to low circulating levels of estradiol by producing more heavily glycosylated molecules that will survive longer in circulation (Wide and Hobson, J. Clin. Endocrinol. Metabol. 56:371 (1983)). Further, the urine would be expected to accumulate only the FSH forms that are able to survive multiple passes through the liver and kidneys and not be removed by the asialyoglycoprotein receptor. The end result is that the FSH present within this commercial preparation exhibits a very prolonged serum half-life.

Although the absolute dose of exogenously administered gonadotropins can be regulated, the heterogeneity of the population within it cannot. When employed to induce follicular growth in infertile women, a number of unwanted effects may occur from the use of a preparation of long-acting FSH forms. The ovaries may become hyperstimulated and the patient may experience discomfort and ascites. The ovaries may hypertrophy to the point that vascular complications arise which can become life threatening. Due to the prolonged half-life of the gonadotropin, this dangerous clinical condition is difficult to manage. A second, more common complication of Pergonal administration is the occurrence of multiple ovulations. The effects of these fertility hormones upon the number of ova shed and subsequently fertilized are well known. The medical, legal and financial complications of hormone-induced multiple births are readily apparent.

To reduce the frequency of occurrence of these unwanted complications while still inducing the ovulation of a single egg, it is important to understand the reproductive endocrine events that occur during this process and attempt to mimic them. The gonadotropin stimulus provided to the ovaries during the follicular phase of the cycle changes in quantity and quality. At the onset of the cycle (at the time of menstruation) the endocrine milieu that surrounds the hypothalamopituitary axis is similar to a hypogonadal state. Serum gonadal steroid concentrations are low and the hypothalamo-pituitary unit responds by an increase in the quantity of FSH to be synthesize and secreted. In addition, the FSH molecule is co- and post-translationally modified such that the majority of the molecules secreted are heavily sialylated and exhibit a prolonged serum half-life. As FSH stimulates folliculogenesis and estradiol biosynthesis during the first fourteen days of the cycle, ovarian hormones (inhibin, gonadal steroids) are secreted into the peripheral circulation and feedback upon the hypothalamo-pituitary axis (Hsueh et al., Endocrine Rev. 5:76 (1984); Chappel et al., Endocrine Rev. 4:179 (1983)). The total amount of FSH to be secreted declines and the type of FSH is altered. The pituitary begins to express forms of FSH that exhibit a much shorter half-life, but a slightly increased receptor binding affinity.

The phenomenon of altered amount and type of FSH secreted has been discovered to be important in the process of the selection of a single dominant follicle. During the very early phase of a new ovulatory cycle, the pituitary FSH signal to the ovaries is long-lived. This acts to stimulate a large crop of primordial follicles to begin the maturational process. As this cohort of follicles begins to develop, they release hormones that signal the pituitary that the follicular growth process has begun. The pituitary responds by secreting an FSH stimulus with a shorter half-life so that only the largest (fastest growing) follicles, with the greatest number of FSH receptors, continue to receive trophic support. As this process proceeds, the largest follicles continue to grow, attract an increased blood supply and continued gonadotropin support, at the expense of the slower maturing follicles. The smaller follicles become atretic and no longer participate in the "follicular wave". After the fourteen day growth period, this process has resulted in the selection of one dominant follicle which proceeds to release one ovum to be fertilized.

When women are treated with exogenous gonadotropins prepared from the urine of post-menopausal women, they receive continuous exposure to a very long-acting form of FSH. Thus, the selection process to produce a single egg is not efficient, and a large number of follicles are able to survive. Since the FSH molecule produced in post-menopausal women (with low circulating levels of gonadal hormones) is predominantly the heavily sialylated form, repeated injection of long-acting FSH allow follicles to survive that ordinarily would not. Thus, the ovary can become overstimulated which may result in multiple ovulations and perhaps births. Ovarian hyperstimulation may also cause discomfort, ascites and cardiovascular complications.

It is another aspect of the present invention to provide a more physiological regimen of gonadotropin replacement to overcome the disadvantages of conventional compositions and regimens.

While more basic and less heavily sialylated forms of FSH might accomplish this, such are not readily available. Because of the presence of infectious agents in human pituitary extracts, that source of basic FSH forms also in unavailable. The only other source, extracts of urine obtained from post-menopausal women, contains very low proportions of the basic forms. Thus, until now it has been impossible to provide a physiologic stimulus to women with preparations heretofore available.

It is yet another aspect to provide a source of basic forms of FSH for use in more physiologically normal therapeutic regimens.

SUMMARY OF INVENTION

In accordance with the principles and aspects of the present invention there are provided novel methods for preparing a more physiologic FSH stimulus to infertile women through the use of recombinant DNA technology and biochemistry. Human FSH is advantageously produced according to the methods detailed in copending patent application of Reddy et al. U.S. Ser. No. 696,647, fully incorporated herein by reference.

Briefly, cDNAs that encode the human alpha and FSH beta subunits are ideally cloned into separate bovine papilloma virus based expression vectors. The mouse metallothionein gene promoter and poly A sequences are provided by the SV40 virus cDNA. Co-transfection of these expression vectors into suitable mammalian cells such as, for example, mouse epithelioid cells (C127) results in the production by such recombinat cells of human FSH that exhibits co- and post-translational modification that is strikingly similar to that observed of FSH found within the anterior pituitary gland. When FSH produced by genetically engineered cells is separated by the technique of isoelectric focusing, all of the forms observed within a normal adult pituitary are observed. This is in striking contrast to the isoelectric focusing profile of FSH present within extracts of urine obtained from post-menopausal females which exhibits an preponderance of acidic forms. These separated forms of FSH are then selectively administered such that the more acid and heavily sialylated forms are given initially and during the therapeutic regimen are gradually changed to smaller quantities of the more basic and lesser sialylated forms. Thus, the most preferred therapeutic compositions of the present invention will comprise recombinant FSH characterized by relatively longer half-life, more sialylation and more acidic isoelectric points followed by one or more step increments by compositions comprising recombinant FSH characterized by relatively shorter half-life, less sialylation and a more alkaline isoelectric point.

DETAILED DESCRIPTION OF THE INVENTION AND BEST MODE

Production of recombinant human FSH U.S. Ser. No. 696, 647, fully incorporated herein by reference provides the nucleotide sequence (as well as deduced amino acid sequence) and procedures for formulating suitable plasmids for transforming mammalian host cells to produce human FSH. Useful in this regard are the deposits of PRF3 ($\alpha$ subunit) in ATCC CRL 8401 and of CRL28FSH2.8BPV ($\beta$FSH) in *E. coli* as NRRLB-15923. While a number of mammalian cells may be chosen for the production of FSH, the most preferred embodiment employs C127 cells tranformed with separate vectors of the $\alpha$ and $\beta$ subunits in a ratio of approximately 1:10. The biologically active heterodimeric human FSH produced by the cells may be purified directly from the cells and/or more preferably, from the culture media which may be removed periodically from cells actively growing in conventional bioreactors.

Preparation of the therapeutic composition of the present invention is advantageously accomplished by subjecting the conditioned medium, obtained from recombinant cells transformed as previously disclosed, to isoelectric focusing. The focused FSH proteins are ideally separated into three zones wherein Zone I has a pI (isoelectric focusing point) value greater than about 5.5; Zone II has a pI value of between about 5.4 and 4.3 and Zone III has a pI value less than about 4.3. While these ranges are preferred in order to derive the ideal "3 step" therapeutic compositions of the present invention, it will be understood that these ranges may be suitably adjusted in order to provide a more refined gradation between the most basic and acidic forms of FSH or a more rapid "two-step" therapeutic composition, as desired.

The FSH present within each of the isoelectric focusing zones is then ideally purified by passage through immunoaffinity columns. While these techniques are well known and need not be described in detail, it is useful to briefly outline the general procedure. Antibodies, most preferably those of monoclonal origin since such have greater specificity and purity than those of polyclonal origin, are covalently attached to a carrier particle such as sepharose beads. Column elements obtained from each of the isoelectric focusing gradients is then applied to separate immunoaffinity columns under conditions allowing immunological reaction between the attached monoclonal antibodies and FSH within the isoelectric focusing column elements. Non-FSH contaminants pass through the column leaving bound FSH which may be subsequently easily eluted under conditions of high salt and low pH.

FSH protein eluted from the immunoaffinity columns is then ideally analyzed for purity by conventional polyacrylamide gel isoelectric focusing, protein staining and Western blotting using monoclonal antibodies directed against the $\alpha$ and $\beta$ subunits of FSH. If purity of the FSH does not rise to a level of at least about 99.5% of the total protein content, an additional purification step comprising HPLC gel filtration is advantageously employed so as to provide a therapeutically acceptable injectable product.

Ideally FSH is presented with therapeutically acceptable carriers (e.g., saline and the like) and formulated in concentration of about 75 International Units per vial in a manner similar to the currently available conventional product. It will be readily apparent that if lyophilization procedures of such vials are to be followed, that suitable stabilizers (e.g., sucrose, maltose and the like) may be necessary in order to improve product shelf life and the ability to reconstitute a therapeutically effective product.

The preferred therapeutic embodiment of the present invention will thus provide for the administration of each of three separate preparations of purified FSH. Each preparation will contain the same amount of FSH (e.g. 75 IU as stated above) but exhibiting different plasma half-lives. The preferred therapeutic administration would comprise administration to the infertile woman for the first three to five days of her ovulatory cycle with preparation III, containing FSH with the longest half-life (e.g., that exhibiting more sialation and having a pI that is more acid). During days 6–10, preparation II, having an FSH preparation with an intermediate plasma half-life, will be administered and during the final days of the follicular phase, preparation I, having FSH exhibiting the short plasma half-life, will be administered.

It will be readily understood by those skilled in the art that numerous departures may be made from the preferred embodiments described herein without departing from either the spirit or scope of the present invention. Specifically, alternative mammalian cells may be employed and transformed with different plasmid constructions utilizing substantially the same DNA sequences described in U.S. Ser. No. 696,647 to produce FSH. Further, there are a variety of reported methods which may be employed for the culturing of such cells, production of FSH, and subsequent purification and, as earlier indicted, the number of zones or isoelectric focusing gradients employed for preparing FSH having varying half-lives may be altered in accordance with the number of preparations desired to be admitted.

What is claimed is:

1. In a method for stimulating follicle development and ovulation in a female patient by administering FSH to said patient during the follicular phase of the ovulatory cycle, the improvement comprising initially administering a first FSH isoform having a relatively long plasma half-life and subsequently administering a second FSH isoform having a shorter plasma half-life.

2. The method of claim 1 wherein said first FSH isoform has an isoelectric focusing point less than about 4.3.

3. The method of claim 1 wherein said first FSH isoform is administered during the first three to five days of the ovulatory cycle.

4. The method of claim 1 comprising administering an intermediate FSH isoform having an intermediate plasma half-life after the administration of the first FSH isoform and prior to the administration of the second FSH isoform.

5. The method of claim 4 wherein said first FSH isoform has an isoelectric focusing point less than about 4.3, said intermediate FSH isoform has an isoelectric focusing point between about 4.3 and 5.4, and said second FSH isoform has an isoelectric focusing point greater than about 5.5.

6. The method of claim 4 wherein said first FSH isoform is administered during the first three to five days of the ovulatory cycle.

7. The method of claim 6 wherein the intermediate FSH isoform is administered during days six to 10 of the ovulatory cycle.

8. The method of claim 7 wherein the second FSH isoform is administered during the final days of the follicular phase of the ovulatory cycle.

9. In a method for stimulating follicle development and ovulation in a female patient by administering FSH to said patient during the follicular phase of the ovulatory cycle, the improvement comprising initially administering an FSH isoform characterized by relatively long plasma half-life, more sialylation and more acidic isoelectric focusing point followed by administering in one or more step increments FSH isoforms of progressively shorter plasma half-life, lesser sialylation, and more alkaline isoelectric focusing point.

* * * * *